US006251587B1

(12) United States Patent
Sévigny et al.

(10) Patent No.: US 6,251,587 B1
(45) Date of Patent: Jun. 26, 2001

(54) METHOD FOR DETERMINING THE PROGNOSIS OF A PATIENT WITH A NEUROLOGICAL DISEASE

(75) Inventors: Pierre Sévigny; Heiko Wiebusch; Keith Schappert, all of Montreal (CA)

(73) Assignee: Nova Molecular, Inc., Montreal (CA)

( * ) Notice: Subject to any disclaimer, the term of this patent is extended or adjusted under 35 U.S.C. 154(b) by 0 days.

(21) Appl. No.: 08/991,850

(22) Filed: Dec. 16, 1997

(51) Int. Cl.$^7$ ............... C12Q 1/68; C12Q 1/00; C12P 19/34; A61K 49/00
(52) U.S. Cl. .................. 435/6; 435/4; 435/91.1; 435/810; 424/9.1
(58) Field of Search ............... 435/6, 91.1, 810, 435/4; 424/9.1

(56) References Cited

U.S. PATENT DOCUMENTS

| | | |
|---|---|---|
| 5,200,324 | 4/1993 | Navaratnam et al. |
| 5,364,793 | 11/1994 | Cameron et al. |
| 5,508,167 | 4/1996 | Roses et al. ............ 435/6 |
| 5,576,022 | 11/1996 | Yang et al. ............ 424/472 |
| 5,583,201 | 12/1996 | Cameron et al. |
| 5,643,960 | 7/1997 | Breitner et al. ............ 514/570 |
| 5,698,224 | 12/1997 | Guittard et al. ............ 424/468 |
| 5,716,828 | 2/1998 | Roses et al. |

FOREIGN PATENT DOCUMENTS

| | | |
|---|---|---|
| 2716894 | 9/1995 | (FR) . |
| 94/09155 | 4/1994 | (WO) . |
| 95/16791 | 6/1995 | (WO) . |
| 95/29257 | 11/1995 | (WO) . |

OTHER PUBLICATIONS

Blumcke et al, "The apolipoprotein E e4 allele is not associated with early onset temporal lobe epilepsy", Neuroreport 8: 1235–1237, 1997.*
Lehtimaki et al, "The frequency of apolipoprotein E4 allele is not increased in patients with probable vascular dementia", Acta Neurol. Scand. 93:352–354, 1996.*
Stone et al., "Astrocytes and Microglia Respond to Estrogen with Increased apoE mRNA in Vivo and in Vitro," *Exp. Neurol.*, 143(2):313–318 (1997).
Bartels et al., "DNA Mutations Associated with the Human Butyrylcholinesterase J–Variant", *Am. J. Hum. Genet.* 50:1104–1114 (1992).
Bartels et al., "DNA Mutation Associated with the Human Butyrylcholinesterase K–Variant and Its Linkage to the Atypical Variant Mutation and Other Polymorphic Sites", *Am. J. Hum. Genet.* 50:1086–1103 (1992).
Bartus et al., "The Cholinergic Hypothesis of Geriatric Memory Dysfunction", *Science* 217:408–417 (1982).
Bertrand et al., "Association of apolipoprotein E genotype with brain levels of apolipoprotein E and Apolipoprotein J(clusterin) in Alzheimer disease", *Mol. Brain. Res.* 33:174–178 (1995).

Boyles et al., "Apolipoprotein E Associated with Astrocytic Glia of the Central Nervous System with Nonmyelinating Glia of the Peripheral Nervous System", *J. Clin. Invest.* 76:1501–1513 (1985).
Brindle et al., "Analysis of the butyrylcholinesterase gene and nearby chromosome 3 markers in Alzheimer disease", *Hum. Mol. Genet.* 7:933–935 (1998).
Corder et al., "Gene Dose of Apolipoprotein E Type 4 Allele and the Risk of Alzheimer's Disease in Late Onset Families", *Science* 261:921–923 (1993).
Goodrum, "Cholesterol Synthesis is Down–Regulated During Regeneration of Peripheral Nerve", *J. Neurochem.* 54:1709–1715 (1990).
Inestrosa et al., "Acetylcholinesterase Accelerates Assembly of Amyloid–62 –Peptides into Alzheimer's Fibrils: Possible Role of the Peripheral Site of the Enzyme", *Neuron* 16:881–891 (1996).
Koo et al., "Obligatory Role of Cholesterol and Apolipoprotein E in the Formation of Large Cholesterol–enriched and Receptor–active High Density Lipoproteins", *J. Biol. Chem.* 260:11934–11943 (1985).
La Du et al., "Phenotypic and Molecular Biological Analysis of Human Butyrylcholinesterase Variants", *Clin. Biochem.* 23:423–431 (1990).
LeBlanc et al., "Regulation of Apolipoprotein E Gene Expression After Injury of the Rat Sciatic Nerve", *J. Neurosci. Res* 25:162–171 (1990).
Lehmann et al., "Synergy between the genes for butyrylcholinesterase K variant and apolipoprotein E4 in late–onset confirmed Alzheimer's disease", *Hum. Mol. Genet.* 6:1933–1936 (1977).
Maekawa et al., "Genetic mutations of butyrylcholine esterase identified from phenotypic abnormalities in Japan", *Clin. Chem.* 43:924–929 (1997).
Masliah et al., "Neurodegeneration in the Central Nervous System of apoE–Deficient Mice", *Exp. Neurol.* 136:107–122, 1995.
Masliah et al., "Apolipoprotein E Role in Maintaining the Integrity of the Aging Central Nervous System", *Springer–Verlag, Heidelberg* pp. 59–73 (1996).
Nalbantoglu et al., "Predictive Value of Apolipoprotein E Genotyping in Alzheimer's Disease: Results of an Autopsy Series and an Analysis of Several Combined Studies", *Ann. Neurol.* 36:889–895 (1994).
Noguchi et al., "Apolipoprotein E genotype and Alzheimer's disease", *The Lancet* (letter) 342:737 (1993).

(List continued on next page.)

Primary Examiner—Jeffrey Fredman
(74) *Attorney, Agent, or Firm*—Clark & Elbing LLP; Kristina Bieker-Brady

(57) ABSTRACT

The present invention provides a method for the determining the prognosis for a patient diagnosed with a neurological disease. The present invention also provides a method for the identification of human subjects for placement in clinical drug trials of drugs being tested for the treatment of neurological disease and for determining a patient's future disease risk.

25 Claims, No Drawings

OTHER PUBLICATIONS

Payami et al., "Apolipoprotein E genotype and Alzheimer's disease", *The Lancet* (letter) 342:737–738 (1993).

Poirier et al., "Apolipoprotein E4 allele as a predictor of cholinergic deficits and treatment outcome in Alzheimer disease", *Proc. Natl. Acad. Sci.* 92:12260–12264 (1995).

Poirier et al., "Cholesterol Synthesis and Lipoprotein Reputake During Synaptic Remodelling in Hippocampus in Adult Rats", *Neuroscience* 55:81–90 (1993).

Poirier et al., "Apolipoprotein E polymorphism and Alzheimer's disease", *The Lancet* 342:697–699 (1993).

Poirier et al., "Apolipoprotein E4, Cholinergic Integrity and Synaptic Plasticity and Alzheimer's Disease", *Springer–Verlag, Heidelberg* pp. 20–28 (1996).

Poirier et al., "Astrocytic apolipoprotein E mRNA and GFAP mRNA in hippocampus after entorhinal cortex lesioning", *Mol. Brain. Res.* 11:97–106 (1991).

Poirier et al., "Cloning of hippocampal poly(A) RNA sequences that increase after entorhinal cortex lesion in adult rat", *Mol. Brain. Res.* 9:191–195 (1991).

Reed et al., "Lower Cognitive Performance in Normal Older Adult Male Twins Carrying the Apolipoprotein E $\epsilon$4 Allele", *Arch. Neurol.* 51:1189–1192 (1994).

Richard et al., "ApoE genotyping and response to drug treatment in Alzheimer's disease", *The Lancet* 349:519 (1997).

Rothe et al., "Uptake of Endoneurial Lipoprotein Into Schwann Cells and Sensory Neurons is Mediated by Low Density Lipoprotein Receptors and Stimulated After Axonal Injury", *J. Neurochem.* 57:2016–2025 (1991).

Russ et al., "K variant of butyrylcholinesterase and late–onset Alzheimer's disease", *The Lancet* 351:881 (1998).

Schellenberg et al., "Genetic Association and Linkage Analysis of the Apolipoprotein CII Locus and Familial Alzheimer's Disease", *Annals of Neurology* 31:223–227 (1992).

Singleton et al., "No association between the K variant of the butyrylcholinesterase gene and pathologically confirmed Alzheimer's disease", *Hum Mol Genet* 7:937–939 (1998).

* cited by examiner

METHOD FOR DETERMINING THE PROGNOSIS OF A PATIENT WITH A NEUROLOGICAL DISEASE

BACKGROUND OF THE INVENTION

The invention relates to a method for determining the prognosis of a patient with a neurological disease.

Neurological diseases include Alzheimer's disease (AD), Creutzfeldt-Jakob disease, Huntington's disease, Lewy body disease, Pick's disease, Parkinson's disease (PD), amyotrophic lateral sclerosis, multiple sclerosis (MS), neurofibromatosis, and diseases without a necessary genetic component such as brain injury, stroke and multi-infarct dementia (MID). Most of these diseases are typified by onset during the middle adult years and lead to rapid degeneration of specific subsets of neurons within the neural system, ultimately resulting in premature death. There are no known cures and few therapies that slow the progression of these diseases.

Parkinson's disease (PD) is a common neurodegenerative disorder which first appears in mid- to late-life. Familial and sporadic cases occur, although familial cases account for only 1–2 percent of the observed cases. The neurological changes which cause this disease are somewhat variable and not fully understood. The disorder generally develops asymmetrically with tremors in one hand or leg and progresses into symmetrical loss of voluntary movement. Eventually, the patient becomes incapacitated by rigidity and tremors. In the advanced stages the disease is frequently accompanied by dementia.

Diagnosis of both familial and sporadic cases of Parkinson's disease can only be made after the onset of the disease symptoms. Anticholinergic compounds, propranolol, primidone and levadopa are frequently administered to modify neural transmissions and thereby suppress the symptoms of the disease, though there is no known therapy which halts or slows the underlying progression.

Multiple Sclerosis (MS) is a neurodegenerative disease of the brain and spinal cord in which a breakdown occurs in the myelin sheathing of the nerve fibers. MS is currently incurable and treatments are few and usually result in only temporary improvements of the disease symptoms.

Stroke is the sudden death of a portion of the brain cells due to a lack of oxygen. A stroke occurs when blood flow to the brain is impaired resulting in abnormal brain function. Brain blood flow can be impaired by blockage or rupture of an artery to the brain.

In the United States, about 400,000 people a year will suffer from a stroke, and up to 40% of these strokes may be fatal. The cost of strokes is not just measured in the billions of dollars lost in work, hospitalization, and the care of survivors in nursing homes. The major cost of a stroke is the loss of independence that occurs in 30% of the survivors. What was a self-sustaining and enjoyable life style may lose most of it's quality after a stroke and family members can often find themselves in a new role as caregivers.

Other cerebral vascular diseases that present similar sequelae to stroke are multi-infarct dementia (MID), vascular dementia (VaD), and cerebrovascular injury or accident. In addition, diseases such as AIDS can often have vascular dementia as a complication. As with the above diseases, there are no known cures for these diseases and most therapies only aid rehabilitation or lower the risk of having another vascular incident.

Apolipoprotein E (apoE) functions as a ligand in the process of receptor mediated internalization of lipid-rich lipoproteins. ApoE is probably also involved in reverse lipid transport. In the central nervous system (CNS), apoE plays a central role in the mobilization and redistribution of cholesterol and phospholipid during membrane remodeling associated with synaptic plasticity. The importance of apoE in the brain is further underscored by the absence of other key plasma apolipoproteins such as apoA1 and apoB in the brain.

The apoE gene on chromosome 19 has three common alleles (E2, E3, E4), which encode three major apoE isoforms. The frequency of the apoE4 allele has been shown to be markedly increased in sporadic Alzheimer's Disease (AD) and late onset familial Alzheimer's disease (AD). This gene dosage effect was observed in both sporadic and familial cases (i.e., as age of onset increases, E4 allele copy number decreases). Women, who are generally at a greater risk of developing Alzheimer's disease, show increased apoE4 allele frequency when compared to age matched men.

The cholinergic hypothesis of geriatric memory dysfunction has raised some fundamental questions regarding the heterogeneity of responses toward different cholinomimetics in AD. The absence of clear beneficial effects of choline and lecithin on geriatric patients with and without AD is still perplexing. Furthermore, multiple clinical studies using esterases inhibitors such as physostigmine and tacrine have shown that, contrary to results found in young subjects, the optimal acute dose necessary to facilitate performance on memory tasks varied considerably among individual aged subjects.

Neurological diseases provide a unique series of complications for the clinicians, patients, and care givers; the diseases often progress rapidly and disrupt a vast number of major life functions. The progressive nature of these diseases makes the passage of time a crucial issue in the choice and administration of different treatment options. It would be desirable to know the severity of the prognosis for patients diagnosed with various neurological diseases.

SUMMARY OF THE INVENTION

We have discovered a method for determining the prognosis of patients with a non-AD neurological disease such as Parkinson's disease, Multiple Sclerosis, or stroke. Our prognostic methods provide a prognosis for the patient, including a prediction of the relative outcome of the patient in terms of rate of progression, severity of disease symptoms, and longevity. The prognostic methods allow clinicians, patients, and family members to make informed choices about therapeutic regimes. This method will also provide for more rapid and cost effective treatment by determining the relative appropriateness of various therapeutic and palliative choices. Even where drug therapy is inappropriate, the prognostic method will provide patients, and their family members, a more informed and realistic expectation of patient outcome including an insight into the most effective rehabilitation strategy, and a forecast of the patient's risk for future disease.

In the first aspect, the invention provides a method of determining the prognosis for a patient diagnosed with a non-AD neurological disease. The method includes: a) identifying a patient already diagnosed with a non-AD disease; b) determining the apoE genotype or phenotype of a patient; and c) converting the data obtained in step b) into a prognosis determination. The prognosis may include a prediction of drug efficacy, patient outcome, and patient risk for future disease events. In preferred embodiments, the method of the invention may further include the steps of determining the BChE genotype or phenotype of a patient, obtaining a patient profile, which may, preferably, include the patient's sex, age, and/or genotype (e.g., presenilin, apolipoprotein E, or BCHE genotype).

In other preferred embodiments of the prognostic method, the patient is diagnosed with a disease selected from the group consisting of: Parkinson's disease (PD), multiple sclerosis (MS), and stroke which shall also include multi-infarct dementia (MID), vascular dementia (VaD), and cerebrovascular injury or accident, for example, as a complication of AIDS.

In a second aspect, the invention provides a method for determining the prognosis of future risks of disease in a asymptomatic mammal. In preferred embodiments the mammal is a human and the method further involves a determination of the mammals BChE genotype or phenotype, obtaining a patient profile, which may, preferably, include the mammal's sex, age, and/or genotype (e.g., presenilin, apolipoprotein E, or BChE genotype).

In a related aspect, the invention provides a kit for performing the prognosis. The kit includes a means for converting the patient profile into a prognosis. In a preferred embodiment, the kit contains a means for performing the steps of the conversion. In another preferred embodiment, the kit contains a means for compiling the data for said patient profile and for formatting said patient profile. In another preferred embodiment, the kit contains a computer software program to perform the data analysis.

It should be noted that the therapies suggested by the prognostic method may be used alone, or in combination with other known therapies that are not otherwise contraindicated for the patient.

For the purpose of the present invention the following terms are defined below. "Non-AD Neurological disease" means any disease other than Alzheimer's disease, which involves the neuronal cells of the nervous system. Specifically included are: prion diseases (e.g, Creutzfeldt-Jakob disease); pathologies of the developing brain (e.g., congenital defects in amino acid metabolism, such as argininosuccinicaciduria, cystathioninuria, histidinemia, homocystinuria, hyperammonemia, phenylketonuria, and tyrosinemia, and fragile X syndrome); pathologies of the mature brain (e.g., neurofibromatosis, Huntington's disease, depression, amyotrophic lateral sclerosis, multiple sclerosis, and stroke); conditions that strike in adulthood (e.g. Creutzfeldt-Jakob disease, Huntington's disease, Lewy body disease, Parkinson's disease, Pick's disease, amyotrophic lateral sclerosis, multiple sclerosis, neurofibromatosis), brain injury, stroke, multi-infarct dementia (MID), vascular dementia (VaD), pathologies of the brain (e.g., brain mishaps, brain injury, coma, infections by various agents, and dietary deficiencies) and, cerebrovascular injury or accident, for example, as a complication of AIDS.

"Drug efficacy" means the a determination of an appropriate drug, drug dosage, administration schedule, and prediction of therapeutic utility.

"Already diagnosed" means already diagnosed as having a neurological disease or having a genetic predisposition or risk for acquiring a neurological disease.

"Patient profile" means data pertaining to the patient for whom the prognostic analysis is being performed. Data may include information on the patient's diagnosis, age, sex, and genotype. The patient's profile may also include materials from the patient such as blood, serum protein samples, cerebrospinal fluid, or purified RNA or DNA.

"Asymptomatic" means that the mammal or human subject has no clinical symptoms of a disease but nonetheless may be a "silent" carrier of a genotype determined by the method of the invention to result later or be likely to result later in the onset of disease symptoms.

"ApoE genotyping" means determination of the type and number of apoE alleles present in the patient, whether determined by nucleic acid sequencing, PCR or RT-PCR amplification, examination of apoE protein, or by other methods available to those skilled in the art.

"Allele load" means the relative ratio of apoE2, 3, and 4 alleles in the patient's chromosomal DNA. The allele load may be determined by comparing the relative numbers of the patient's already known apoE allele types.

"PCR or RT-PCR amplification" means subjecting a DNA sample to a Polymerase Chain Reaction step or an RNA sample to a Reverse Transcriptase-Polymerase Chain Reaction step, such that, in the presence of appropriately designed primers, a DNA fragment is synthesized or fails to be synthesized and thereby reveals the allele status of a patient.

"BChE genotype" means a determination of the patient's alleles that encode the butyrylcholinesterase gene product. This may be accomplished by nucleic acid sequencing, RT-PCR, PCR, examination of the BChE protein, a determination of the BChE enzyme activity, or by other methods available to those skilled in the art.

"BCHE-K allele" means the polymorphism of the butyrylcholinesterase (BChE) gene which has a point mutation at nucleotide 1615 that changes amino acid residue 539 from alanine to threonine and can result in an enzyme with reduced catalytic activity. Other polymorphisms of this locus exist (e.g., deletions (BCHE*FS4), missense mutations (BCHE*24 M, *1005, *250P, *267R, *3301, *365R, *418S, *515C, *539T), and nonsense mutations (BCHE*119STOP, *465STOP)) and are included within the scope of the invention.

"Prognosis" means a method whereby diagnostic data, including the patient's neurological diagnosis and genetic data, such as the patient's apoE and BChE genotype, are processed to provide therapeutic options and prognoses. Processing may include, but not be limited to, the collection of a patients medical history including age and sex, apoE and BChE genotyping using appropriately designed primers and using a RT-PCR or PCR amplification step, apoE and BChE phenotyping using an antibody-mediated method or enzymatic test, and statistical analysis step that converts this raw data into a prognosis. The prognosis may include a prediction of a patient's response to drug therapy, recovery time, age of disease onset, treatment efficacy, rehabilitation time, symptomology of attacks, and risk for future disease. For example, a high apoE4 allele load could be used as a positive predictor for stroke patients that respond well under drug therapy and as negative predictor of PD and MS patient response to drug therapy. A prognosis may also be determined for asymptomatic and healthy subjects in order to forecast future disease risks an determine what preventive therapies should be considered or invoked in order to lessen these disease risks. The prognosis may include the use of a computer software program to analyze patient data and run statistical cross-checks against relational databases that are constantly being updated.

DETAILED DESCRIPTION OF THE INVENTION

Here we show that a correlation of age, sex, apoE genotype, and BChE genotype, may be used to formulate a prognosis for a given patient with a neurological disease.

The prognosis can include a prediction of both relative age of onset, rate of disease progression, and risk for future disease.

We have investigated the relationship between the apoE4 genotype and cholinergic deficits, and we observed that the greater the number of apoE4 alleles the lower the apoE level. Furthermore, reduction in ChAT activity in the hippocampus and temporal cortex of AD cases is inversely proportional to the apoE4 allele copy number (i.e. where the apoE4 allele copy number is increased the ChAT activity is decreased). In addition, we found that another presynaptic marker of cholinergic projection, the nicotinic receptor, was markedly reduced in apoE4 AD subjects. Conversely, we have found that a typical post-synaptic marker, M1-muscarinic receptor, is unaltered in AD versus non-AD subjects, irrespective of whether apoE4 is present or not. The M2-muscarinic receptor, a composite pre- and post-synaptic marker, is also unaffected by the apoE4 allele gene dosage. We have also observed that the presence of the apoE4 allele lowers the age of onset of neurological disease and worsens the prognosis.

The above findings clearly indicate the existence of distinct genetic entities in neurological disease which correlate with differential degrees of alterations of cholinergic innervation. In turn, the innervation level correlates with the prognosis, including the ability to respond to cholinomimetic drugs.

We believe the correlation between apoE4 allele load and reductions in ChAT activity and nicotinic receptors may be explained by at least two distinct phenomena. First, phospholipids such phosphatidylcholine (PC) and phosphatidylethanolamine (PE), that can serve precursors to choline in the synthesis of acetylcholine (Ach), could be transported into neurons via the classical apoE-LDL receptor pathway. An isoform-dependent impaired regulation of the transport of phospholipids in the brain of apoE4 carriers could explain the reduced levels of PC, PE and choline reported in AD (Pettegrew J. W., 1989, Ann. NY Acad. Sci., 568:5–28; Nitch R M et al., 1992, Proc. Natl. Acad. Sci., 89:1671–1675). This, in turn, may lead to decreased Ach synthetic capacities. This hypothesis is consistent with membrane defects reported in AD subjects such as changes in membrane fluidity in the hippocampus and in the platelets of AD patients. The loss of cholesterol reported in AD and the effect of apoE4 on nicotinic binding activity are consistent with the apoE4/impaired lipid homeostasis hypothesis.

In addition to the above, the reduction in neuronal ChAT activities and choline levels in both AD and non-AD patients could parallel the loss of cholinergic neurons. The analysis of the number of acetylcholinesterase-positive neurons in the nucleus basalis of Meynert (NBM) and the diagonal band of Broca (DBB) in AD patients revealed marked losses of cholinergic neurons in apoE4 carriers versus apoE3 homozygous AD cases.

Although these observations were initially made in AD patients, we have discovered that our observations regarding apoE allele load and drug therapies can be generalized to non-AD neurological diseases because the underlying mechanism altered by the apoE allele load is not AD-specific. Our discovery indicates that the apoE4 allele load, taken together with patient profile parameters, can predict individual variations in a patients response to drug treatment, rehabilitation, and risk for future disease. The method of the invention provides useful predictions for patients with diseases such as stroke, Parkinson's disease, and Multiple Sclerosis as discussed in the Examples herein. Prospective-retrospective analyses of patients that are either good or poor responders to drugs designed to ameliorate the conditions of stroke, Parkinson's disease, and Multiple Sclerosis, (e.g., aspirin, antithrombotics, ticlopidine (Ticlid™), levodopa-carbidopa, (Sinemet™) and interferon β-1B (Betaseron™)) are presented in the Examples. We further propose that the method of the invention also can be used to generate prognostic protocols for other cerebral vascular injuries that involve similar disease mechanisms to stroke. Such diseases would include multi-infarct dementia (MID), cerebrovascular injury, brain injury, or cerebral vascular pathologies as a complication AIDS.

The prognostics method is useful for allowing the physician to select the most appropriate drug, drug dosage, administration or palliative therapy for a patient. The invention also provides a method for forecasting future patient disease risk. This forecast method allows the patient and clinician to consider and invoke preventive therapeutic regimens before disease strikes or to at least lower the risk of future disease events.

The present invention will be more readily understood by referring to the following examples which are given to illustrate the invention rather than to limit its scope.

EXAMPLE I

Methods and Study Design

Determination of apoE Levels and Allele Load

Genotype analysis for each patient was performed using high molecular weight DNA, or alternatively RNA, isolated from 5 mls of whole blood drawn from each patient. The apoE genotype was determined using an allele-specific primer extension method. Primers labeled D, E, F, G, and H were synthesized by Genosys Biotech (The Woodland, TX) using primer sequences provided in Main et al. (Main R.F. et al., 1991, J. Lipid. Res., 32:183–187). Reactions were carried out in a volume of 51 uL containing 1 ug of DNA; deoxyadenosine triphosphate, deoxycytidine triphosphate, deoxythymidine triphosphate and deoxyguanosine triphosphate, each 0.2 mmol/L; 10% dimethyl sulfoxide; 12.5 pmol of either primer D, E, F, or G; 25 pmol of primer H; and 10 uL of 10× PCR reaction buffer (Vector Biosystem, Toronto, ONT.). The DNA in the reaction mixture was first denatured for 10 min. at 96° C. and then cooled to 4° C. One unit of Taq polymerase (Vector Biosystem, Toronto, ONT.) was then added to each sample. Each sample was reheated for 2 min. at 96° C. and subjected to 30 cycles in a thermal cycler with each cycle consisting of a 10 sec denaturation at 96° C., 30 sec annealing at 58° C., and 1 min. extension at 65° C. The reaction products were visualized by electrophoresis of 10 uL of the reaction mixture in a 1% agarose gel containing TPE buffer (0.08 mol/L Tris-phosphate, 0.002 mol/L EDTA, Sigma, St-Louis, USA) and ethidium bromide (0.15 ug/mL) for 1 hr at 67 v. The gels were then photographed and the banding profile was compared to known standards.

Alternatively, the apoE phenotype can be determined in a patient using a serum or cerebrospinal fluid sample. Proteins are size separated on a 25 cm SDS polyacrylamide gel (10%) and transferred onto a nitrocellulose filter using a BIO-RAD™ Trans-blot cell and detection of the apoE protein is performed using a polyclonal antibody raised against human apoE protein (International Immunology Corp., CA, Dil. 1:2000). To control for antibody specificity, adsorption of the anti-apoE antibody with purified human apoE protein (MW 34–36 kDa) is performed see if will specifically block apoE detection. Molecular weight markers (Rainbow markers, Amersham) are run in adjacent wells while visualization of the bands is done with a chemiluminescence detection kit (Amersham, Cat. No. RPN 2100). Quantification of the autoradiographic signals is performed using a MCID image analysis system (Ste-Catherine, Ontario) equipped with the ID-gel analysis software.

Patients who completed the drug trial were selected for a determination of their apoE genotype as previously described (above and Poirier et al., 1993, Lancet 342:697–699). Patients were examined for the impact different apoE genotypes (e.g., 2/2, 3/2, 3/3, 3/4, 2/4 and 4/4) had on a patient's response to drug therapy, recovery time, age of disease onset, treatment efficacy, rehabilitation time, symptomology of attacks, and risk for future disease.

EXAMPLE II

Relationship Between ApoE Genotype and Drug Therapy Outcome in Patients Suffering from Stroke We have analyzed 51 patients suffering from stroke to determine if there is a relationship between apoE genotype and drug therapy outcome. Our small study group was composed of Caucasian females, currently diagnosed as suffering from stroke, and currently under treatment with either aspirin or anti-thrombotic drugs (e.g. Ticlid™). Although our study group is small, and is not randomized by sex, the patients in this study have a apoE allele distribution similar to a much larger randomized North American-population (see Table 1). To determine a patients apoE genotype, 5 mls of whole blood was drawn from each patient and used as a source of genetic material for apoE allele determination as described in Example I. The patient's apoE genotype was then compared with information from the patient's medical file. We have measured the speed at which patients recover from a stoke incident and the duration of their rehabilitation, in order to assess the potential relationship between a patient's apoE genotype and stroke prognosis.

Results

TABLE 1 apoE Allele Distribution of Study Group Compared to Representative Population

| Genotype | % Population (Canada) | Study Group |
|---|---|---|
| E4/E4 | 3.9% | 0% |
| E4/E3 | 20.6% | 27% |
| E4/E2 | 9.8% | 2% |
| E3/E3 | 61.8% | 59% |
| E3/E2 | 2.0% | 12% |
| E2/E2 | 2.0% | 0 |

In order to determine the relationship between apoE genotype and the time it takes a patient to make a complete recovery from a stroke incident, we have analyzed the data as follows. We have divided the study group into two populations, those patients which recovery quickly on drug therapy (fast responders) and those patients that recovery slowly on drug therapy (slow responders) and asked what is the apoE allele representation (Table 2).

TABLE 2 apoE Genotype Distribution in Stroke Patients that Make a Complete Recovery Under Drug Therapy Quickly vs. Slowly

| Genotype | % population (Canada) | This Study | Slow Responder | | Fast Responder |
|---|---|---|---|---|---|
| E4/E4 | 3.9% | 0% | 0% | | 0% |
| E4/E3 | 20.6% | 27% | 20% | → | 47% |
| E4/E2 | 9.8% | 2% | 3% | | 0% |
| E3/E3 | 61.8% | 59% | 63 | ← | 47% |
| E3/E2 | 2.0% | 12% | 14% | ← | 7% |
| E2/E2 | 2.0% | 0% | 0% | | 0% |

When the genotypes of these two populations were compared, we observed a link between the speed of recovery from stroke and being a carrier of the apoE4 allele. The fastest responders to drug therapy following stroke, were patients carrying the apoE4 allele (Table 2). When these data were analyzed as a function of apoE4 allele load, patients with a greater apoE4 allele load were over represented as making a good recovery (Table 3).

TABLE 3

Comparison of apoE4 Genotype Load and Stroke Recovery

| Genotype | poor | | good |
|---|---|---|---|
| +E4 | 19% | → | 32% |
| −E4 | 81% | ← | 68% |

In order to determine the relationship between apoE genotype and age of disease onset, apoE genotype data was analyzed as a function of the age of the patient when the first stroke incident occurred (Table 4). In this study, the majority of the patients, 74%, were non-apoE4 carriers, and the genotypes were well distributed into all age groups, which minimized any favored results due to longevity possibly being linked to apoE genotype.

TABLE 4 apoE4 Allele Distribution as a Function of Age When Patient Suffered Stroke Incident

| Genotype | 50–60 | 70 | 80 | 90 |
|---|---|---|---|---|
| E4/E4 | 0.0% | 0.0% | 0.0% | 0.0% |
| E4/E3 | 22.2% | 20.0% | 30.8% | 66.7% |
| E4/E2 | 11.1% | 0.0% | 0.0% | 0.0% |
| E3/E3 | 66.7% | 73.3% | 53.8% | 16.7% |
| E3/E2 | 0.0% | 6.7% | 15.4% | 16.7% |
| E2/E2 | 0.0% | 0.0% | 0.0% | 0.0% |

In addition, analysis of this data by age group does not show major differences regarding treatment efficacy, even though, patients in the 70 year old group appear to have the best overall response to drug treatment (Table 5).

TABLE 5

Drug Treatment Efficacy for Stroke Patients as a Function of Age

| | % Study | 50–60 | 70 | 80 | 90 |
|---|---|---|---|---|---|
| Poor | 100% | 15% | 31% | 31% | 8% |
| Average | 100% | 18% | 18% | 36% | 14% |
| Good | 100% | 23% | 46% | 8% | 15% |
| Very good | 100% | 0% | 50% | 0% | 0% |

In order to determine if the apoE genotype influences the total time a stroke patient requires for rehabilitation (a long rehabilitation period after a stroke incident is common), we have analyzed patient rehabilitation time as a function of the patient's apoE genotype. We observed a direct and positive relationship between the presence of an apoE4 allele and a short rehabilitation time (Table 6).

TABLE 6

Total Rehabilitation Time Required after Stroke Incident as a Function of Patient apoE Genotype

| Genotype | % Population (Canada) | % Study | Quick | | Slow |
|---|---|---|---|---|---|
| E4 | 15.20% | 21% | 28% | ← | 19% |
| E3 | 77% | 69% | 64% | → | 74% |
| E2 | 7.80% | 10% | 8% | | 7% |

In order to assess whether a patient's apoE genotype influences recovery directly after a stroke attack, we have analyzed a patient's ability to make an immediate recovery following stroke as a function of the patient's apoE genotype. We observed that the speed of recovery immediately following a stroke attack is not apoE genotype dependent (Table 7).

TABLE 7

Patient Recovery Ability Immediately Following a Stroke as a Function of Patient apoE Genotype

| Genotype | % population (Canada) | % Study | Quick | Slow |
|---|---|---|---|---|
| +E4 | 15.2% | 21% | 21% | 25% |
| −E4 | 84.8% | 79% | 79% | 75% |

In summary, we have discovered that a direct link exists between the presence of an apoE4 allele and a stroke patient's outcome. We believe that the apoE4 allele may be beneficial to the stroke patient. We further predict, that the ability to upregulate the expression or stability of the apoE4 gene product, may have beneficial consequences for a patient suffering from stroke. This invention proposes that the ability of a drug to increase apoE4 gene expression or stability would implicate that drug as a therapeutically-effective drug for patients with stroke.

EXAMPLE III

Relationship Between ApoE Genotypes and Drug Therapy Outcome in Patients Suffering from Parkinson's Disease We have analyzed 59 patients suffering from Parkinson's disease (PD) to determine if there is a relationship between a patient's apoE genotype and drug therapy outcome. Our small group was composed of Caucasian males, diagnosed as suffering from PD, and currently under treatment with levadopa-carbidopa (Sinemet™). These patients were not suffering from any other central nervous system disease. To determine the patient's apoE genotypes, 5 mls of whole blood was drawn from each patient and used as a source of genetic material for apoE allele determination as described in Example I. The patient's apoE genotype was then compared with information from the patient's medical file. Our analysis was based on comparing patient response to a drug treatment designed to improve symptoms of tremor and rigidity, as a function of the patient's apoE genotype.

Results

TABLE 8

ApoE Genotype Distribution of Study Group, a Larger Population, and Across Different Age Groups

| Genotype | % population (Canada) | % Study | 40–50 | 60 | 70 | 80 |
|---|---|---|---|---|---|---|
| E4 | 15.20% | 16.3% | 18.8% | 10.7% | 20.0% | 0.0% |
| E3 | 77% | 68.8% | 68.8% | 71.4% | 70.0% | 100.0% |
| E2 | 7.80% | 15.0% | 12.5% | 17.9% | 10.0% | 0.0% |

Although our study group is small, and is not randomized by sex, the patients in this study have an apoE allele distribution similar to a much larger randomized North American-population (Table 8). We also observed a similar apoE allele distribution among different age groups, suggesting that apoE genotype is not linked to longevity (Table 8). We compared the average age of patients who responded well to drug therapy (good responder) versus those patients that did poorly (bad responder), and observed a similar average age (64–67). This result further confirmed the lack of an age component in this data set. Furthermore, analysis of the apoE allele load between good and bad responders to drug therapy revealed that age differences did not influence treatment outcome.

In contrast, we observed a strong negative correlation between patient response to drug therapy and apoE4 allele load. Patients with no apoE4 allele showed a better response, as measured by improvements in symptoms of rigidity and tremor, then did those patient's with an apoE4 allele (Table 9). Thus, we conclude that a negative correlation for patients carrying an apoE4 allele and treatment outcome for Parkinson's Disease.

TABLE 9

Drug Response of Parkinson's Disease Patients with Different apoE Genotypes

| Genotype | % population (Canada) | % Study | Bad responder | | Good responder |
|---|---|---|---|---|---|
| E4/E4 | 3.9% | 0% | 0% | | 0% |
| E4/E3 | 20.6% | 17% | 20% | ← | 8% |
| E4/E2 | 9.8% | 5% | 4% | | 4% |
| E3/E3 | 61.8% | 63% | 68% | → | 72% |
| E3/E2 | 2.0% | 14% | 4% | → | 16% |
| E2/E2 | 2.0% | 2% | 4% | | 0% |
| +E4 | 15.2% | 16% | 18% | ← | 9% |
| −E4 | 84.8% | 84% | 81% | → | 91% |

EXAMPLE IV

Relationship Between ApoE Genotype and Drug Therapy Outcome in Patients with Multiple Sclerosis We have analyzed 65 patients suffering from multiple sclerosis (MS) to determine if there is a relationship between the patient's apoE genotype and drug therapy outcome. Our small group was composed of Caucasian females, diagnosed as suffering from MS, and currently under treatment with interferon β-1B (Betaseron™). To determine a patient's apoE genotype, 5 mls of whole blood was drawn from each patient and used as a source of genetic material for apoE allele determination as previously described (see Example I). The patient's apoE genotype was then compared with information from the patient's medical file. Our analysis was based on comparing a patient's response to drug treatment for symptomatic MS exacerbations as a function of the patient's apoE genotype.

Results

We analyzed the frequencies of apoE genotypes in our study group as compared to a larger representative population. We observed that the patients in this study had an apoE allele distribution similar to a much larger randomized North American-population (Table 10). We also observed a similar distribution among different age groups suggesting that the apoE genotype is not linked to longevity (Table 10).

TABLE 10

ApoE Genotype Distribution of Study Group, Larger Population, and Amongst Different Age Groups

| Genotype | % population (Canada) | % study | <30 | 30–40 | >40 |
|---|---|---|---|---|---|
| E4 | 15.20% | 15.6% | 9.7% | 21.6% | 12.5% |
| E3 | 77% | 66.7% | 67.7% | 62.2% | 68.8% |
| E2 | 7.80% | 17.8% | 22.6% | 16.2% | 18.8% |

In order to determine the relationship between a patient's apoE genotype and a patient's response to drug therapy designed to lessen the symptomatic flare-ups of MS, we have analyzed the data as follows. We have divided the study group into two populations representing those patients which have fewer attacks on drug therapy (good responders) and those patients that have many attacks while on drug therapy (bad responders) and asked what is the apoE allele representation (Table 11). We have observed that non-apoE4 patients responded better to drug therapy than did those patients that carried an apoE4 (Table 11).

TABLE 11

ApoE Genotype Distribution in MS Patients Responding Well to Drug Therapy Versus Those Patients Responding Poorly

| Genotype | % population (Canada) | % study | Bad responders | | Good responders |
|---|---|---|---|---|---|
| E4/E4 | 3.9% | 0.0% | 0.0% | | 0.0% |
| E4/E3 | 20.6% | 15.4% | 8.3% | | 8.3% |
| E4/E2 | 9.8% | 6.2% | 6.9% | ← | 1.7% |
| E3/E3 | 61.8% | 60.0% | 23.3% | → | 33.3% |
| E3/E2 | 2.0% | 16.9% | 5.0% | → | 13.3% |
| E2/E2 | 2.0% | 1.5% | 1.7% | | 0.0% |

When we analyzed these MS patients by apoE4 allele presence, the correlation between those patients that respond well and the lack of an apoE4 allele is striking (Table 12). Lack of an apoE4 allele is clearly predictive of a good response to drug therapy.

TABLE 12

ApoE4 Allele Load in MS Patients Responding Well to Drug Therapy Versus Those Patients Responding Poorly

| Genotype | % population (Canada) | % study | Bad | | Good |
|---|---|---|---|---|---|
| +E4 | 15.2% | 16.5% | 6.7% | ← | 5.6% |
| −E4 | 84.8% | 65.9% | 20.0% | → | 43.3% |

In another analysis of MS patients, we studied the correlation between a patient's apoE4 allele load and the qualitative nature of the patient's MS attacks each year while undergoing drug treatment. The following results are subdivided into 8 groups, representing patient's with mild attacks reacting badly to treatment compared with patients with mild attacks having a good response to treatment, and patients with severe attacks compared in the same manner (Table 13). We observed that an apoE4 allele load had a negative impact on the efficacy of drug treatment for MS patients as measured by a diminution in the number of worsening attacks (Table 13). Thus, we conclude that an apoE4 allele load is a strong predictor of poor MS patient response to drug treatment.

TABLE 13

ApoE4 Allele Load in MS Patients with a Qualitative Change in Attacks

| Genotype | mild-bad | | mild-good | severe-bad | | severe-good |
|---|---|---|---|---|---|---|
| +E4 | 3% | | 2% | 5% | | 7% |
| −E4 | 15% | → | 34% | 14% | → | 20% |

We believe these results demonstrate that the Apolipoprotein E gene is not only linked to the drug efficacy in Alzheimer's disease, but also directly related to drug efficacy in different CNS diseases such as stroke, Parkinson's disease, and Multiple Sclerosis. Due to the specific role of the apoE gene and its proposed role in cell regeneration and plasticity requirements specific to a disease, we predict that the disease relevant genotype will vary from disease to disease.

EXAMPLE V

Determination of Risk Prognosis and Therapeutic Treatment Outcome of Stroke Events Using Genetic Analysis of apoE4 and BCHE-K Stroke is an acute neurologic event leading to death of neural tissue of the brain and resulting in loss of motor, sensory, and/or cognitive function. It is said to be the third leading cause of death in the United States. Genetic predisposition may be important in the pathogenesis of stroke. Such predisposition may not only include genes contributing to elevated blood pressure but also genes acting independently of blood pressure. Twins studies and familial aggregation support evidence for genetic factors contributing to stroke with a polygenic aetiology.

Genetic factors contributing to stroke pathogenesis are poorly established. The following genes and polymorphisms have been implicated in stroke: ACE insertion/deletion polymorphisms, factor V gene, factor VII gene, PIA2 polymorphism of the glycoprotein IIIa gene, ApoE, and the interleukin 1β converting enzyme (ICE) gene family.

Butyrylcholinesterase (BChE) is expressed in most human tissues, but its precise metabolic function in the body is still unknown. The polymorphic gene variant BCHE-K, consisting of a point mutation at nucleotide 1615 (GCA to ACA) which changes alanine 539 to threonine, has reduced catalytic activity (Bartels et al., Am. J. Hum. Genet. 50:1086–1103, 1992). Recent research from Lehmann et al. (Hum. Mol. Genet. 11: 1933–1936 (1997)) suggests that BCHE-K is associated with a further increase in the risk of late-onset AD in apoE4 carriers.

We have discovered that the combination of apoE4 and BCHE-K contribute to define an individual's risk for the development of stroke. We have determined the ApoE4 and BCHE-K genotype for 50 female stroke patients and 64 age and sex matched healthy controls (Table 16). In the control group, we observed 17 out of 64 subjects were heterozygous for the BCHE-K allele, and 4 out of 64 subjects were homozygous carriers of the BCHE-K allele. We observed that 15 out of 64 subjects carried one copy of the apoE4 allele. Both of these allele distributions fit a Hardy-Weinberg equilibrium for the identified allele frequency (Table 14). In the stroke patients group, 22 out of 50 subjects carried one copy of BCHE-K, and 3 out of 50 subjects were observed to carry two BCHE-K alleles. Of these 50 subjects, 15 were carriers of one apoE4 allele. The identified carrier status was in agreement with a Hardy-Weinberg population for the observed allele frequency (Table 14).

TABLE 14

Allelic Frequencies of apoE4 and BCHE-K

|  | No. of subjects | F:M ratio | mean age | AF BCHE-K | AF ApoE4 |
|---|---|---|---|---|---|
| controls >58 years | 64 | F only | 72 | 0.195 | 0.117 |
| Stroke cases | 50 | F only |  | 0.28 | 0.15 |
| p = (X-square, Yates corr.) |  |  |  | 0.18 (NS) | 0.6 (NS) |

For subjects 58 years of age and older, the allelic frequency of BCHE-K was 0.195 in controls and 0.28 in the 50 stroke cases, providing an odds ratio of stroke of 1.6 (based on allele frequencies) and 2.1 (based on carrier frequencies) (Table 17.). In ApoE4 carriers, the odds ratio of stroke was about 1 (Table 15).

TABLE 15

Odds Ratios of Stroke for BCHE-K alleles

| subjects | controls | cases | Odds ratio (alleles) | 95% CI | Odds ratio (carriers) | 95% CI |
|---|---|---|---|---|---|---|
| all | 64 | 50 | 1.6 | 0.9–2.9 | 2.1 | 1.0–4.4 |
| ApoE4 carriers | 15 | 15 |  |  | 1.3 | 0.3–5.6 |

The allelic frequency of apoE4 was 0.12 in controls and 0.15 in 50 stroke cases, giving an odds ratio of stroke of 1.3 (based on allele frequencies) and 1.4 (based on carrier frequencies) (Table 16). In BCHE-K carriers, the odds ratio of stroke was 1.9 (calculated for carrier status) (Table 16).

TABLE 16

Odds Ratios of Stroke for apoE4 alleles

| subjects | controls | cases | Odds ratio (alleles) | 95% CI | Odds ratio (carriers) | 95% CI |
|---|---|---|---|---|---|---|
| all | 64 | 50 | 1.3 | 0.6–2.8 | 1.4 | 0.6–3.2 |
| BCHE-K carriers | 21 | 25 |  |  | 1.9 | 0.5–7.2 |

Taking account of the carrier status of both gene mutations, we have discovered that there is a two fold increase (8% vs 18%) in stroke cases, compared to controls, in carriers with both the apoE4 and BCHE-K allele (Table 17). This trend is also seen in the apoE4 carriers.

TABLE 17

Proportion of Control and Stroke Subjects with both BCHE-K and apoE4 Alleles

| subjects | Controls | Stroke cases | P = (X-square, Yates corr.) |
|---|---|---|---|
| all | 5/64 (8%) | 9/50 (18%) | 0.17 (NS) |
| ApoE4 carriers | 5/15 (33%) | 9/15 (60%) | 0.27 (NS) |

In Table 18, we provide the odds ratio of stroke for subjects carrying at least one allele of apoE4 and BCHE-K as compared to control subjects who have neither allele. In female subjects over 58 years of age who carry both the apoE4 and BCHE-K alleles, the odds ratio of sustaining a stroke was 2.8 fold higher than age matched controls. These data predict for female carriers of this genetic status, an almost 3 fold higher risk for stroke.

TABLE 18

Odds Ratio of Stroke

| ApoE4 | BCHE-K | controls | Stroke | Odds ratio (carriers) | 95% CI |
|---|---|---|---|---|---|
| no | no | 33 | 21 | Reference |  |
| yes | yes | 5 | 9 | 2.8 | 0.9–9.2 |

In summary, we have discovered that determining an individuals's apoE4 and BCHE-K allele status is a useful tool in the prediction of an individual's risk for stroke. Furthermore, our results demonstrate that prognostic forecasting could allow patients to start prophylactic therapies before disease strikes. For example, the risk of stroke could be calculated for asymptomatic and healthy individuals as young adults and well before a stroke incident has occurred. Then as the individual ages, preventive therapies could be invoked in order to prevent or lessen the likelihood of a catastrophic stroke incident later in life.

OTHER EMBODIMENTS

While the invention been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

Other embodiments are within the claims.

What is claimed is:

1. A method of determining the prognosis for a patient already diagnosed with one of the following neurological diseases: Parkinson's disease, multiple sclerosis, or stroke, said method comprising:

a) identifying a patient with said disease;

b) determining the apoE genotype or phenotype of said patient;

c) converting the data obtained in step b) into a prognosis for said patient.

2. The method of claim 1, wherein said prognosis includes a prediction of drug efficacy, patient outcome, or a forecast of patient disease risk.

3. The method of claim 1, wherein the method further comprises determining the BChE genotype or phenotype of said patient.

4. The method of claim 1, wherein said method further comprises obtaining a patient profile.

5. The method of claim 4, wherein said patient profile includes a determination of said patient's sex.

6. The method of claim 4, wherein said patient profile includes the genotype of said patient.

7. The method of claim 4, wherein said patient profile includes the age of said patient.

8. A method for identifying a patient in a clinical trail of a drug for the treatment of one of the following neurological diseases: Parkinson's disease, multiple sclerosis, or stroke, said method comprising:
   a) identifying a patient already diagnosed with said disease or as being predisposed to acquire or be at risk for said disease;
   b) determining the apoE genotype or phenotype of said patient;
   c) converting the data obtained in step b) and determining the prognosis of said patient, said prognosis including a prediction of whether the patient is a candidate for a drug trial for the treatment of said disease.

9. The method of claim 8, wherein said method further comprises determining the BChE genotype or phenotype of said patient.

10. The method of claim 8 wherein said drug is from the group comprising antithrombotics, cholinomimetics, dopaminergics, and interferon β-1B.

11. The method of claim 8 wherein said drug is tacrine.

12. The method of claim 8 wherein said patient is asymptomatic.

13. A method of determining a prognosis of future risk of a neurological disease, selected from the group consisting of Parkinson's disease, multiple sclerosis, and stroke, for a mammal asymptomatic for said disease, said method comprising:
   a) determining the apoE genotype or phenotype of said mammal;
   b) converting the data obtained in step a) into a prognosis for said mammal, said prognosis including a prediction of said mammal's future disease risk, drug treatment efficacy for said disease, or treatment outcome.

14. The method of claim 13, wherein said mammal is a human.

15. The method of claim 13, wherein the method further comprises determining the BChE genotype or phenotype of said mammal.

16. The method of claim 13, wherein said method further comprises obtaining a patient profile of said mammal.

17. The method of claim 16 wherein said patient profile includes a determination of said mammal's sex.

18. The method of claim 16, wherein said patient profile includes the genotype of said mammal.

19. The method of claim 16, wherein said patient profile includes the age of said mammal.

20. The method of claim 1, wherein the presence of at least one apoE4 allele worsens said prognosis.

21. The method of claim 1, wherein said patient is diagnosed as having stroke or as being predisposed to sustain a stroke.

22. The method of claim 1, wherein said patient is diagnosed as having Parkinson's disease or as being predisposed to acquire Parkinson's disease.

23. The method of claim 1, wherein said patient is diagnosed as having multiple sclerosis or as being predisposed to acquire multiple sclerosis.

24. The method of claim 8, wherein said drug is levodopa-carbidopa.

25. The method of claim 8, wherein said drug is selected from the group consisting of aspirin and ticlopidine.

* * * * *

UNITED STATES PATENT AND TRADEMARK OFFICE
CERTIFICATE OF CORRECTION

PATENT NO.    : 6,251,587 B1
DATED         : June 26, 2001
INVENTOR(S)   : Pierre Sévigny, Heiko Wiebusch and Keith Schappert It is certified that error appears in the above-identified patent and that said Letters Patent is hereby corrected as shown below:

Title page,
Item [73], Assignee, replace "Nova Molecular, Inc." with -- Variagenics, Inc., Cambridge, (MA) --;
Item [56], References Cited, U.S. PATENT DOCUMENTS, insert -- 6,022,683 2/08/01 Poirier 435/4 --;
OTHER PUBLICATIONS, within the Inestrosa et al. reference title, replace "Amyloid-62 -Peptides" with -- Amyloid-β-Peptides --;
Within the LeBlanc et al. reference title, replace "*Res*25:162-171" with -- *Res* 25:162-171 --;
Item [57], ABSTRACT,
Line 1, replace "for the determining" with -- for determining --;

Column 3,
Line 4, replace "BCHE" with -- BChE --;

Column 4,
Line 23, replace "BCHE" with -- BChE --;
Line 55, replace "risks an determine" with -- risks and determine --;

Column 5,
Line 31, replace "such" with -- such as --;

Column 6,
Line 11, replace "AIDS." with -- of AIDS --;
Line 64, replace "if will" with -- if it will --;

Column 7,
Line 31, replace "a apoE" with -- an apoE --;
Line 64, replace "which recovery" with -- that recover --;
Line 65, replace "recovery" with -- recover --;

Column 11,
Line 67, replace "patient's with" with -- patients with --;

UNITED STATES PATENT AND TRADEMARK OFFICE
CERTIFICATE OF CORRECTION

PATENT NO. : 6,251,587 B1
DATED : June 26, 2001
INVENTOR(S) : Pierre Sévigny, Heiko Wiebusch and Keith Schappert It is certified that error appears in the above-identified patent and that said Letters Patent is hereby corrected as shown below:

Column 14,
Line 40, replace "invention been described" with -- invention has been described --; and Column 16,
Line 22, replace "as having stroke" with -- as having a stroke --.

Signed and Sealed this

Tenth Day of December, 2002

JAMES E. ROGAN
*Director of the United States Patent and Trademark Office*